United States Patent [19]

Tucker et al.

[11] Patent Number: 5,436,456
[45] Date of Patent: Jul. 25, 1995

[54] MOISTURE METER CURVE CALIBRATION SYSTEM

[75] Inventors: Billy J. Tucker; Carl C. Beeler, both of Macon, Ga.

[73] Assignee: Brown & Williamson Tobacco Corporation, Louisville, Ky.

[21] Appl. No.: 133,534

[22] Filed: Oct. 7, 1993

[51] Int. Cl.⁶ .............................................. G01N 21/35
[52] U.S. Cl. .................. 250/341.5; 250/339.1
[58] Field of Search ............... 250/339.1, 341, 340, 250/341.1, 341.5

[56] References Cited

U.S. PATENT DOCUMENTS 5,163,454 11/1992 Clemons .................. 131/302

OTHER PUBLICATIONS

Willard et al "Instrumental Methods of Analysis" Pub. Van Nostrand Co. 1981 p. 932.

*Primary Examiner*—Paul M. Dzierzynski
*Assistant Examiner*—Richard Hanig
*Attorney, Agent, or Firm*—Charles I. Sherman

[57] ABSTRACT

A system for calibrating moisture meters by comparing data from a plurality of infrared moisture meters with data from analytical moisture tests for a plurality of blends of tobacco, wherein a computer is programmed to perform a statistical analysis on the resultant data to produce a calibration curve for each moisture meter for each blend of tobacco, and where the calibration curve is automatically transferred to a control system programmed to apply the corresponding calibration curve to raw data from the moisture meter to provide corrected meter data for affecting control of the tobacco handling process.

7 Claims, 2 Drawing Sheets

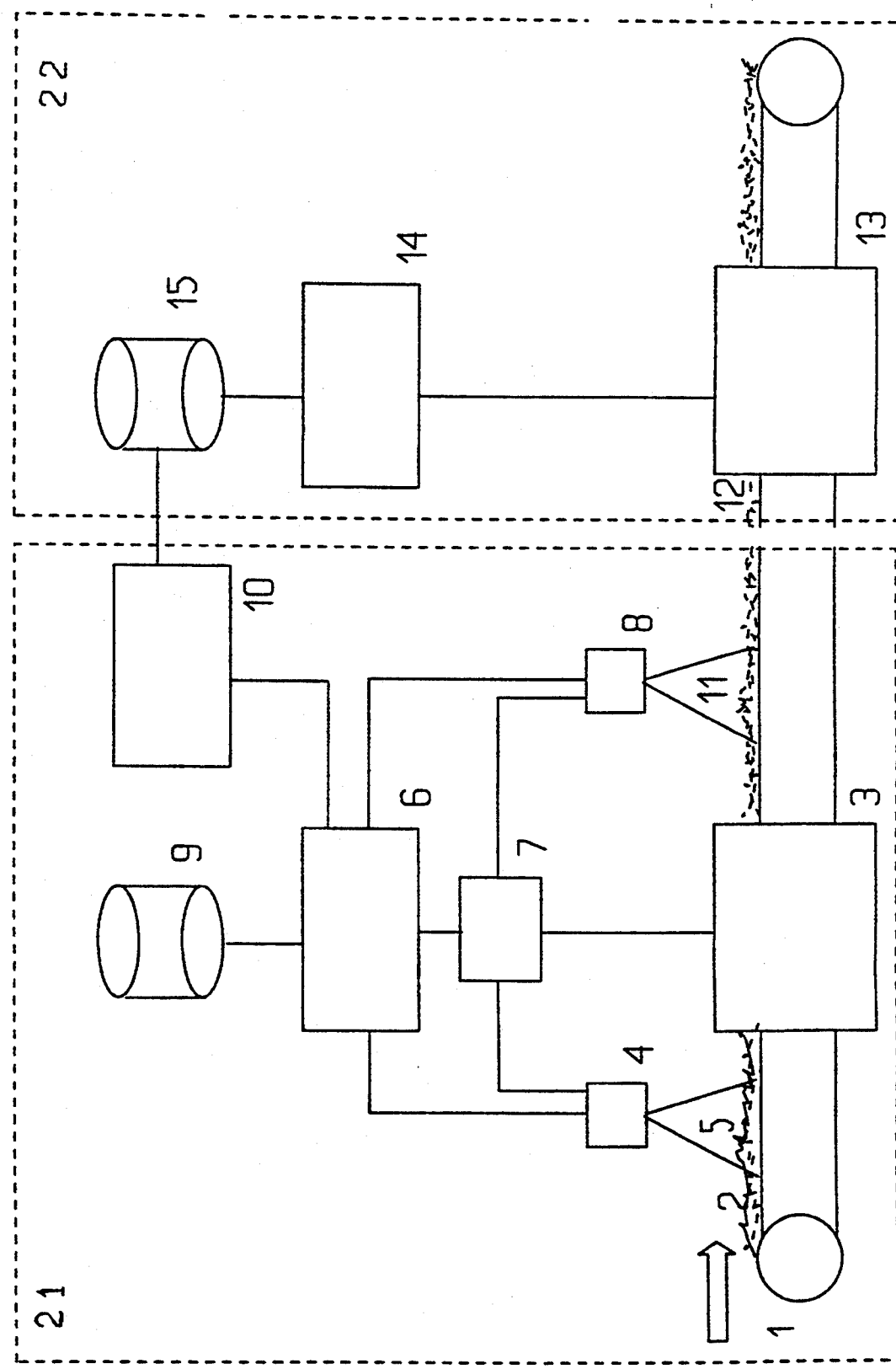

MOISTURE METER CURVE CALIBRATION SYSTEM

BACKGROUND OF THE INVENTION

This invention relates to a system for maintaining desired moisture levels in cut tobacco during the process of drying the tobacco. Particularly, this invention relates to comparing data from a plurality of infrared moisture meters with data from analytical moisture tests for a plurality of blends of tobacco, wherein a statistical analysis is performed on said data to produce a calibration curve for each moisture meter for each blend of tobacco. This calibration curve data is automatically transferred to a control system programmed to control the process of drying, where the raw data coming from each moisture meter is adjusted in accordance with the calibration curve for each blend of tobacco before the meter data is used to control further processing of the tobacco.

In the tobacco industry, the determination of moisture content of cut tobacco is of critical importance. Frequently, the moisture content of tobacco leaf is measured with a reflectance-type infrared absorption meter, which determines the water content of the tobacco by measuring its infrared reflectance in response to two beams of light in the near infrared region. One of the beams of light is within one of several infrared wavelength bands characteristic of water absorption (i.e., 0.8–2.5 microns). The other beam of light is just outside whatever wavelength band that is used for the first beam. The difference in the reflectance values of the two beams is a function of the moisture content of the sample.

Because of drift characteristics commonly seen in metering circuitry, moisture meters must be recalibrated periodically to verify that the low and high readings have not changed from a standard. Calibration may be accomplished by comparing a meter's response to a standard material having known reflectance values, and either adjusting the meter or devising a corrected scale in response thereto. Typically, a meter is adjusted for regulation of a span between the "0" point on the instrument and the upper reach of values to meet technical specifications in a given range of physical measurements. Some commercially supplied standard test materials include simple black-and-white reflectance disks that are intended to provide reproducible low and high reflectance values. However, black-and-white reflectance testing has generally been found unsatisfactory due to uncontrolled specular and diffuse reflections. Instruments may also be calibrated using actual samples of a particulate matter that are believed to cover the range of desired moisture content. U.S. Pat. No. 4,082,950 to Chen teaches a calibration assembly where the reflective sample material is sandwiched between two etched glass plates and is used for comparison to calibrate a meter for the desired range.

Another type of calibration relies upon a statistical comparison of metered and laboratory-tested data to produce a cross-reference table, or "calibration curve," which expresses a linear relation between the meter readings of the subject matter and the readings of a know comparable matter, in order to adjust the meter. Typically, a calibration curve is derived by comparing meter readings from several samples to laboratory test results on the same samples, where each reading measures the same characteristics of the matter so as to construct a cross reference relationship. Mathematically, a calibration curve may be graphed as a smooth curve connecting a series of calibration points that relate the experimentally determined test sample data to the electronically determined meter values. Because of minor variations from one meter to another, a unique calibration curve must be calculated for each meter. In addition, the calibration curve for each meter must be further calibrated with each blend of tobacco.

U.S. Pat. No. 4,864,842 to Regimand teaches a method and system for transferring calibration data to nuclear gauges in the field that are used to measure neutron moderating characteristics of sample materials, such as asphalt-aggregate paving mix. Regimand teaches the cross-referencing of output from field gauges to output from a master gauge adjusted to a known standard to create a calibration curve. This curve data may be manually entered into the memory of a field gauge to avoid the necessity of individually transporting the gauges back to the laboratory for calibration.

SUMMARY OF THE INVENTION

The present invention is directed to a moisture meter curve calibration system for use in a tobacco handling apparatus to calibrate infrared absorption moisture meters to insure that tobacco moisture is maintained within uniform and defined limits for each blend of tobacco during a drying process. Basically, in the present invention moisture meters send electrical analog signals to a computer where the signals are converted to digital values and stored on a computer along with selected batch information identifying a particular blend of tobacco. During tobacco processing, such as drying, test samples of the aforementioned batch are grabbed from the processing line, baked in an oven and weighed to determine the moisture content at selecting processing points. Test data is recorded from each batch of tobacco at selected processing points and correlated to electrically obtained readings from the moisture meter. A computer program analyzes both sets of data for purposes of creating a matching curve which the control system can use to adjust the raw data from the moisture meters before further controlling the drying process. The control system is programmed to use the adjusted data, then, rather than the raw data, to further automate a tobacco handling process.

More particularly, the present invention involves a tobacco handling system for calibrating the infrared metering means that provides data to the process control means used to monitor the moisture content of tobacco. The invention comprises a moisture metering means for measuring the moisture content of a batch of tobacco at a plurality of processing points; a tobacco moisture sampling means, said sampling means including means to grab tobacco samples at selected processing points and determine the moisture content thereof; a computer system, including a computer programmed to capture, analyze, and distribute data from the moisture metering means and the sampling means, said computer program including means to perform a statistical analysis and produce a calibration curve correlating data from the metering means and the sampling means; a computer programmed to calculate the calibration curve; and a programmable logic controller programmed to administer the curve to the raw data for controlling the tobacco handling process responsive to the adjusted meter data.

Even more particularly, the present invention is part of a tobacco handling system, where raw signals received from infrared moisture meters reading a plurality of blends of tobacco are calibrated before said meter signals are passed to process control means used to maintain the moisture content of the tobacco within defined limits. The invention is comprised of an infrared metering means for measuring the moisture content of the tobacco at a plurality of locations along a conveyor line moving cut tobacco; a manual sampling means using analytical test procedures to determine the moisture content of the tobacco from selected batches; a network means for transferring data from the infrared metering means and manual sampling means to a computer; a computer programmed to read the meter data and test sample data, and perform a statistical analysis thereon to produce a calibration curve; a process controller programmed to correct raw meter data before the data is used by the process control means to control the process of drying the tobacco; and, process control means responsive to the corrected data to control process operations of the tobacco handling.

BRIEF DESCRIPTION OF THE DRAWINGS

A better understanding of the present invention will be had upon reading the following description in conjunction with the accompanying drawings, wherein:

FIG. 2 is a flow diagram of a tobacco drying operation including the moisture meter calibration system of the present invention.

DETAILED DESCRIPTION OF A PREFERRED EMBODIMENT

1. Overview

Figure 1:
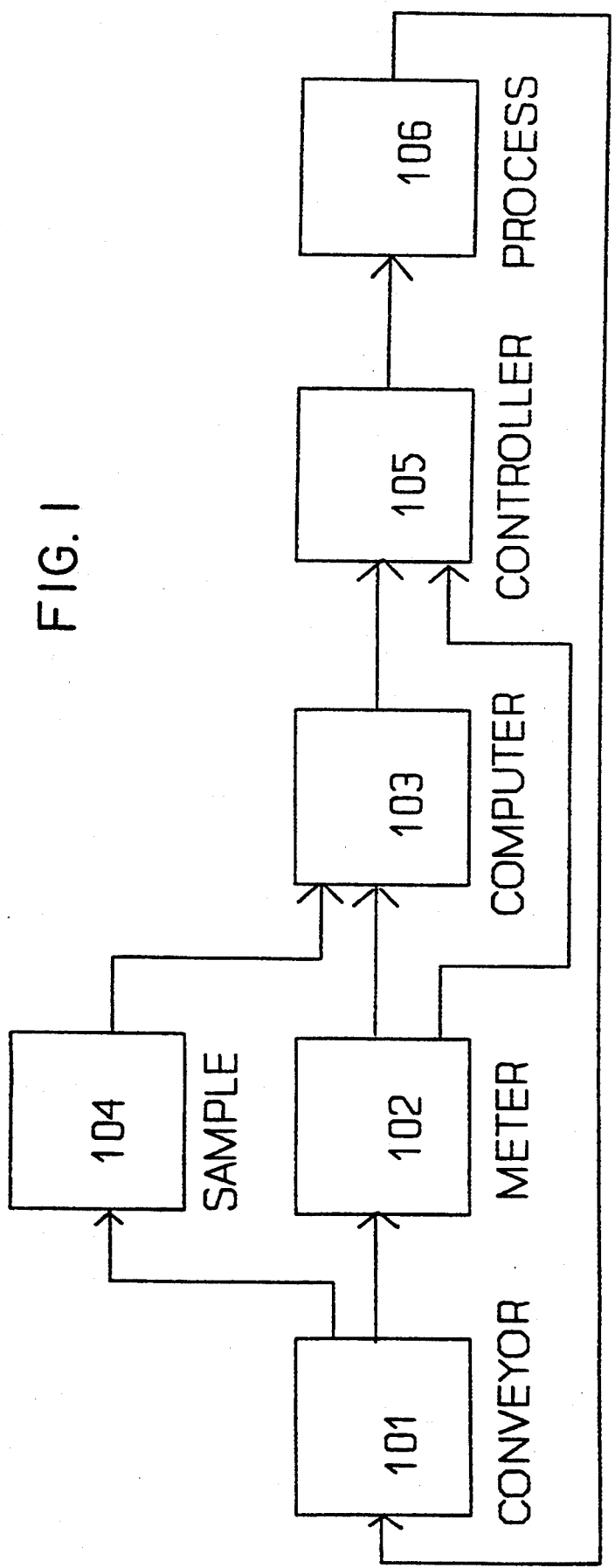
FIG. 1 is a block diagram of a moisture meter calibration system.

FIG. 1 shows a block diagram of the overall flow of product and information in the present invention for calibrating a moisture meter in a tobacco processing system. The blocks 101, 102, 103, 104, and 105 represent the high-level interrelationships of different operations involved in monitoring of the moisture content in a batch of tobacco. For example, as the tobacco moves along conveyor 101, at various preselected locations the tobacco is scanned by an infrared moisture meter 102 which sends a reading to a computer 103. A sample of the tobacco is also manually grabbed off the line as noted by numeral 104 and laboratory tests are conducted and results therefrom entered into a computer 103. Computer 103 is programmed to calculate a calibration curve correlating the data from moisture meter 102 and the manual sampling means 104. The calibration curve data is passed to a controller 105, which then applies the curve to raw data coming directly from moisture meter 102 to control a selected tobacco handling process 106. This conceptual overview is grossly simplified, but serves as a general introduction to the following two data captive stages, the process control stage and the quality control stage, and thereafter computerized analysis and automated calibration.

2. Process Control Stage

In the process control stage 21 as shown in FIG. 2, a vibrating conveyor identified by the numeral 1, is provided to convey particulate matter, such as tobacco 2, in the direction identified by the arrow through a process zone, such as, for example, a drying chamber 3. An infrared absorption moisture meter 4, such as, for example, a model manufactured by Quadrabeam, is located directly above the tobacco in a scanning area 5. Meter 4 is positioned above the tobacco at a height of approximately five to six inches and is located just before the conveyor enters the drying chamber 3. The moisture meter 4 employs conventional infrared absorption monitoring means to measure the infrared reflectance of the tobacco directly below it. The moisture meter 4 reads the tobacco at intervals of approximately every six seconds and produces an analog signal representing the infrared reflectance level of the tobacco. This analog signal is passed to a computer 6, such as, for example, a Hewlett-Packard model 200 (hereinafter identified as the moisture control computer), where it is converted to a digital value using conventional digitizing circuitry, such as, for example, a digitizer board manufactured by Allen Bradley, and stored. Concurrently, programmable logic controller (PLC) 7, which controls operations in drying chamber 3, provides to computer 6 selected information concerning the batch identification of the tobacco then being processed, including batch ID number, date, time, and blend of tobacco. The moisture control computer 6 is programmed to combine the digital values from moisture with meter 4 the batch information from PLC 7 to create a moisture meter data record. This moisture meter record is stored in a moisture meter database 9, residing on moisture meter computer 6 and backed up on a backup computer 10 such as a Hewlett Packard Model 400, all of which are shared resources in a network based on a multiuser, multitasking operating system such as UNIX, making the moisture meter database 9 accessible to other computers on the network.

As mentioned above, a plurality of moisture meters 4 may be embodied in this invention, but for illustration purposes herein, only two moisture meters 4 and 8 will be described. Thus, in the process control stage 21 shown in FIG. 2, a second moisture meter 8 is shown located at the exit of drying chamber 3, directly over scanning area 11 at the same height from the tobacco at meter 4. At the same intervals, analog infrared reflectance signals are output from moisture meter 8 and passed to the moisture control computer 6, where they are similarly digitized, stored, and merged with batch information from PLC 7, and also written to the moisture meter database 9. In the present invention, raw data from moisture meters 4 and 8 is also directly passed to PLC 7, where said raw data is first adjusted according to the appropriate calibration curve held in PLC 7, as described below, before being displayed on an operator console or used for control of the tobacco drying process.

3. Quality Control Stage

Downstream from the above-described process control stage 21, the tobacco passes through a quality control stage 22 where laboratory technicians perform tests on samples of dried or processed tobacco 12 to measure the moisture content thereof. Using the "grab sample" method, handfuls of tobacco 12 are grabbed off conveyor 1 as a batch moves through a quality control or sampling station 13. The sample is first weighed, then the moisture is removed by oven baking at a temperature of approximately 110° degrees for approximately 2.75 hours. After oven baking, the samples are weighed again, with the difference being a measure of the moisture content of the tobacco sample. This moisture content number, along with the corresponding batch ID information, is keyed into another computer 14, such as a Hewlett-Packard model 200 (hereinafter identified as the quality control computer), which is programmed to write a quality control record to the quality control database 15. The quality control database 15 is manually reviewed daily, then automatically transferred, via the network to the moisture control computer 6, for subsequent processing in the moisture control system. The moisture control computer 6 is programmed to read and compare the quality control database 15 and the moisture meter database 9, and produce a cross-reference table, or calibration curve, by programming steps described below. The network embodied in the present invention may consist of one or more computers operating under a multiuser, multitasking operating system, such as UNIX, with timed polling procedures and high-speed communications for making data generally available to other computers on the network in a timely manner.

4. Calibration Curve

Because different blends of tobacco have different moisture content characteristics, a unique calibration curve must be calculated for each blend of tobacco and for each moisture meter. The moisture control computer 6 is programmed to read and match the moisture meter database 9 and the quality control database 15 and to perform a statistical analysis thereon using historical averages and standard deviations for each moisture meter for each blend of tobacco. (See Table 1) In the process control stage 21, moisture meters 4 and 8 may typically provide numerical values in a range, say of 500 to 1,000. A running sum of the values from each meter for each batch is accumulated and an average reading is determined for a meter for a batch, as well as the standard deviation of error from the mean. Subsequently,

TABLE 1

| | Meter 4 | | | | Meter 8 | | | | Quality Control | | |
|---|---|---|---|---|---|---|---|---|---|---|---|
| Batch | Num | Avg | Est | SD | Num | Avg | Est | SD | Num | Avg | SD |
| 115 | 396 | 691 | 12.2 | 93 | 396 | 691 | 12.2 | 93 | 5 | 12.8 | 0.6 |

Where:
"Batch" is the ID for the particular batch of tobacco
"Num" is the number of samples taken from that source
"Avg" is the average reading. For Quality Control, this is percent moisture, for Meters 4 and 8, this is the average of the raw data from the meters
"Est" is the percent moisture calculated from the raw data and the existing span using the formula % Moisture = Zero + (Span*Raw)
"SD" is the standard deviation from the Avg during the quality control stage 22, several grab samples and oven baking tests may be taken per batch and the resultant analytical data, in the form of a percentage of moisture content, which typically may be in the range of 10% to 15%, is manually entered into quality control computer 14. An average percentage of moisture content per batch is determined, as well as the standard deviation of error from the mean. Historical averages are kept for each meter and for each blend. The metering average is divided by the sampling average to give a correction factor expressed as a percentage, which is eventually applied to raw meter readings to give a corrected reading. The estimated moisture percentage is calculated according to the following equation:

$$\% \text{ MOISTURE} = \text{ZERO} + (\text{SPAN} * \text{RAW})$$

where
% MOISTURE is the estimated moisture percentage
ZERO is the existing zero for the meter
SPAN is the existing span for the meter
RAW is the average of the raw data from the meter As each new blend of tobacco in introduced into the production flow and assigned a batch ID number, each moisture meter must be recalibrated. Accordingly, the calibration curve data associated with each moisture meter for each particular blend of tobacco is automatically downloaded from the calibration curve database 9 into the memory of the controller, PLC 7, that is controlling the process zone in which these moisture meters are operating. PLC 7 checks its memory for a calibration curve for each moisture meter for that blend, and corrects the incoming raw data from the meter before further processing the raw data for system control purposes. As PLC 7 receives the raw data from the moisture meters 4 and 8, it is programmed to apply the matching curve for that meter blend, and multiply the raw data value by the calibration curve, and send the corrected data to the operator and to the moisture control system logic for further processing.

Referring to FIG. 2, when a new batch is started, the matching curve is automatically downloaded by the computer 6 to PLC 7, which is programmed to adjust the raw signals coming from moisture meter 4 in accordance with the calibration curve prior to interpreting those signals for system control. Likewise, the appropriate calibration curve is downloaded to PLC 7 for moisture meter 8, so that when signals are received from moisture meter 8 they are automatically corrected according to the calibration curve loaded for that current blend of tobacco.

The foregoing detailed description is given primarily for the clearness of understanding and no unnecessary limitations are to be understood therefrom for modifications can be made by those skilled in the art reading this disclosure and may be made without departing from the spirit of the invention and scope of the appended claims herein.

What is claimed is:

1. In a tobacco handling apparatus, a system for automatically calibrating at least one moisture meter used to monitor the moisture content of at least one tobacco blend, comprising:
    a conveyor for transporting tobacco past a scanning area;
    at least one moisture meter for measuring the infrared reflectance values of said tobacco blend in said scanning area, said at least one moisture meter coupled to a computer by a network to provide data for a meter database;
    sampling means for experimentally measuring the moisture content of said tobacco to provide data for a sample database;
    a computer operably connected to said network and centrally storing said meter database and said sample database, said computer programmed to respond to said meter database and said sample database to calculate a calibration curve and enter said calibration curve into a calibration curve database for each of said at least one moisture meter and each of said at least one tobacco blend;

a programmable logic controller operably connected to said at least one moisture meter and connected to said computer by said network and responsive to a calibration curve downloaded from said calibration curve database stored on said computer and adjusting said meter data from said at least one moisture meter according to said calibration curve to control said tobacco handling apparatus.

2. A method of automatically calibrating a moisture meter used to measure the moisture content of tobacco, comprising:

conveying tobacco past a scanning area;

providing meter signals from said moisture meter to measure the moisture content of tobacco in said scanning area to provide a meter database;

sampling said tobacco and testing said tobacco for moisture content to provide a sample database;

storing on a computer said meter database and said sample database;

programming said computer to correlate said meter database and said sample database to calculate a calibration curve and enter said calibration curve into a calibration curve database; and programming a programmable logic controller connected by network to said computer and said moisture meter to automatically receive a calibration curve from said calibration curve database and correct said meter signals in response to said calibration curve for control of said tobacco handling apparatus.

3. The method of claim 2 further comprising a meter database, sample database and calibration curve database for a plurality of tobacco blends allowing said meter to be calibrated automatically for each of said plurality of tobacco blends.

4. The method of claim 3 wherein calibrating of said meter for a particular blend of tobacco occurs automatically.

5. The method of claim 2 wherein said shared computer resources allows for connecting a plurality of said meters used to measure moisture content of tobacco and wherein said plurality of meters are automatically calibrated for each of said particular blends of tobacco.

6. A moisture meter calibration system, comprising:

a vibrating conveyor for conveying a plurality of tobacco blends;

a plurality of infrared absorption moisture meters located above said vibrating conveyor;

a programmable logic controller operably connected to said plurality of infrared absorption moisture meters and controlling said vibrating conveyor;

a computer operably connected to said programmable logic controller and to said plurality of infrared absorption moisture meters;

a moisture meter database stored on said computer of measured moisture content data for each of said plurality of infrared absorption moisture meters in said calibration system;

a sample database stored on said computer of actual moisture content for each of said plurality of tobacco blends;

wherein said computer is programmed to calculate a calibration curve for each of said plurality of infrared absorption moisture meters and for each of said plurality of tobacco blends from said data on said moisture meter database and said sample database;

whereby said programmable logic controller loads said calibration curve for each infrared absorption meter connected to said programmable logic controller for the tobacco blend currently on said conveyor and adjusts the measured moisture content received from each of said moisture meters.

7. A method of automatically calibrating a plurality of infrared moisture meters used to measure the moisture content of tobacco, comprising:

conveying tobacco past a scanning area on a conveyor;

controlling said conveyor using a programmable logic controller;

scanning said tobacco with said plurality of infrared moisture meters;

providing signals representing the moisture content of said tobacco read by said plurality of moisture meters to create a meter database;

manually sampling said tobacco to provide actual moisture content data and entering said actual moisture content into a sample database for each of said plurality of tobacco blends;

calculating a moisture meter calibration curve utilizing said meter database and said sample database for each of said plurality of infrared moisture meters and for each of said plurality of tobacco blends supported;

identifying which of said plurality of tobacco blends is being scanned in said scanning area;

providing to said programmable logic controller a calibration curve for each of said plurality of infrared moisture meters connected to said programmable logic controller for the tobacco blend being scanned;

adjusting said signals by said programmable logic controller generated by each of said plurality of moisture meters connected to said programmable logic controller with said calibration curve.

* * * * *